(12) United States Patent
Yoshida et al.

(10) Patent No.: US 7,489,395 B2
(45) Date of Patent: Feb. 10, 2009

(54) METHOD AND APPARATUS FOR INSPECTING PATTERN DEFECTS

(75) Inventors: Minoru Yoshida, Yokohama (JP); Shunji Maeda, Yokohama (JP); Atsushi Shimoda, Hiratsuka (JP); Kaoru Sakai, Yokohama (JP); Takafumi Okabe, Yokohama (JP)

(73) Assignee: Hitachi High-Technologies Corporation, Ltd., Tokyo (JP)

( * ) Notice: Subject to any disclaimer, the term of this patent is extended or adjusted under 35 U.S.C. 154(b) by 0 days.

(21) Appl. No.: 11/518,195

(22) Filed: Sep. 11, 2006

(65) Prior Publication Data

US 2007/0002318 A1 Jan. 4, 2007

Related U.S. Application Data

(63) Continuation of application No. 11/192,021, filed on Jul. 29, 2005, now Pat. No. 7,110,105, which is a continuation of application No. 10/218,463, filed on Aug. 15, 2002, now Pat. No. 6,927,847.

(30) Foreign Application Priority Data

Sep. 13, 2001 (JP) ............................. 2001-277681

(51) Int. Cl.
*G01N 21/00* (2006.01)
(52) U.S. Cl. ................. 356/237.5; 356/237.2; 250/365; 250/503.1; 250/504 R
(58) Field of Classification Search ........................ None
See application file for complete search history.

(56) References Cited

U.S. PATENT DOCUMENTS

| | | | |
|---|---|---|---|
| 4,634,240 A | 1/1987 | Suzuki | |
| 5,774,222 A | 6/1998 | Maeda et al. | |
| 6,031,607 A | 2/2000 | Miyazaki | |
| 6,084,716 A | 7/2000 | Sanada | |
| 6,091,488 A | 7/2000 | Bishop | |
| 6,288,780 B1 | 9/2001 | Fairley et al. | |
| 6,369,888 B1 | 4/2002 | Karpol et al. | |
| 6,621,571 B1 | 9/2003 | Maeda et al. | |
| 6,900,888 B2 | 5/2005 | Yoshida | |
| 6,927,847 B2 | 8/2005 | Yoshida | |

FOREIGN PATENT DOCUMENTS

| | | |
|---|---|---|
| JP | 59-226317 | 12/1984 |
| JP | 62-231924 | 10/1987 |
| JP | 07-318326 | 12/1995 |
| JP | 08-320294 | 12/1996 |
| JP | 10-078668 | 3/1998 |

*Primary Examiner*—Gregory J Toatley, Jr.
*Assistant Examiner*—Juan D Valentin
(74) *Attorney, Agent, or Firm*—Antonelli, Terry, Stout & Kraus, LLP.

(57) ABSTRACT

A method and apparatus for inspecting pattern defects emitting a laser beam, adjusting a light-amount of the laser beam, converting the light-amount adjusted laser beam into a slit-like laser light flux, lowering coherency of the slit-like laser light flux, and irradiating a sample with the coherence reduced slit-like laser light flux. An image of reflection light from the sample is obtained, and a detector is provided which includes the image sensor for receiving the image of the reflection light and for converting it into a detected image signal. An image processor is provided for detecting defects on patterns formed on the sample in accordance with the detected image signal.

22 Claims, 16 Drawing Sheets

METHOD AND APPARATUS FOR INSPECTING PATTERN DEFECTS

CROSS REFERENCE TO RELATED APPLICATIONS

This application is a continuation application of U.S. application Ser. No. 11/192,021, filed Jul. 29, 2005, now U.S. Pat. No. 7,110,105, which is a continuation application of U.S. application Ser. No. 10/218,463, filed on Aug. 15, 2002, now U.S. Pat. No. 6,927,847, the contents of which are incorporated by reference, and is related to U.S. application Ser. No. 10/650,756, filed Aug. 29, 2003, now U.S. Pat. No. 6,900,888, and U.S. application Ser. No. 11/131,379, filed May 18, 2005.

BACKGROUND OF THE INVENTION

The present invention relates to inspection of patterns and/or foreign matters, for detecting or examining defects, such as short-circuit and/or open-circuit or the like, on the patterns as a target of inspection, and relates, in particular, to a method and an apparatus, for inspecting the defects and/or foreign matters of the patterns formed on, such as, a semiconductor wafer, a liquid crystal display, and a photo-mask, etc., for example. Hereinafter, it is assumed that the defects include the foreign matters, in the meaning thereof.

Conventionally, in such kind of an inspection apparatus, as is described in Japanese Patent Laying-Open No. Hei 7-318326 (1995) <hereinafter, conventional art 1>, an image is detected on the patterns to be examined or inspected by means of an image pick-up element, such as a line sensor, etc., while moving the patterns to be inspected, so as to compare an image signal detected with one which is delayed by a predetermined time in gradation thereof, thereby acknowledging inconsistency or anti-coincident to be a defect.

Also, other conventional art, relating to the defect inspection of patterns to be inspected, is known from Japanese Patent Laying-Open No. Hei 8-320294 (1996) <hereinafter, conventional art 2>. In this conventional art 2 is described a technology, for examining the patterns to be inspected, for example, a semiconductor wafer, in which areas high pattern density, such as the memory mat portions, etc., and low pattern density, such as peripheral circuit portions, etc., are mixed with each other, wherein gradation conversion is conducted on digital image or video signal, which is obtained through A/D conversion of the image signal detected, so that a predetermined relationship can be established between the high density areas and the low density areas on the patterns to be inspected, in particular in the brightness or the contrast thereof, rather than the frequency distribution thereof, and this image signal converted in gradation is compared with other gradation conversion image signal for comparison, under the condition of being fitted to each other in position, thereby inspecting minute or microscopic defects thereon with high accuracy.

Furthermore, the conventional art for inspecting the patterns on a photomask is already known, for example, Japanese Patent Laying-Open No. Hei 10-78668 (1998) <hereinafter, conventional art 3>. In this conventional art, it is described that the UV light rays are irradiated upon the mask, equally, in which coherence is lowered by rotating a diffuser panel inserted within an optical path, with using a UV laser beam as a light source, such as, an excimer laser or the like, so as to calculate out a characteristic amount or quantity from the obtained image data of the mask, thereby deciding or examining good or bad, i.e., the quality thereof. And, a projection exposure apparatus with using an excimer laser therein is already known, for example, in Japanese Patent Laying-Open No. Sho 59-226317 (1964) or Japanese Patent Laying-Open No. Sho 62-231924 (1987), etc.

For LSI manufacturing in recent years, the circuit patterns formed on a wafer come to be minimized, such as, 0.25 µm or less than that in the pattern width thereof, responding to the needs of high integration; thus it nearly reaches up to the limit on the resolving power of an image-forming optical system. For this reason, development is advanced on application of high NA technology or an optical super resolving power technology.

However, the NA technology also reaches up to the limit thereof, physically. Accordingly, a substantial or intrinsic approach is trying to shift the light wavelengths to be applied for the detection into the regions of the UV light and DUV light, i.e., shortening the light wavelength.

Further, due to the necessity of conducting the inspection with high speed, it is impossible to adopt the method of scanning the laser beam focused or converged thinly on a sample. On the contrary, when trying to illuminate with irradiating the laser beam spreading out all over a visual field, however the illumination of the laser beam generates speckles, or an overshoot or an undershoot, being called by a "wringing", at an edge portion of the circuit pattern, thereby bringing about a problem that the image cannot be obtained of good quality.

SUMMARY OF THE INVENTION

An object, according to the present invention, for dissolving such the drawbacks of the conventional arts mentioned above, is to provided a method and an apparatus, for inspecting or examining the microscopic circuit patterns with high resolving power at high speed, thereby achieving inspection of the defects.

Also, other object, according to the present invention, is to provide a manufacturing method of semiconductor devices, with applying the method and the apparatus for inspecting the pattern defects mentioned above, thereby enabling the manufacture of the super microscopic semiconductor devices.

According to the present invention, in a pattern defects inspecting apparatus using a UV light source or a UV laser beam source as a light source, being provided with a light-amount adjustment optical system for adjusting a light-amount of the UV light or the UV laser beam and a coherence reduction optical system for suppressing generation of speckles of the UV light or the UV laser beam, in an optical path thereof, wherein the UV light lowered in coherency is irradiated upon the surface of a target, thereby detecting an image of the target to be inspected. Herein, the UV light includes a DUV light therein.

Namely, according to the present invention, a pattern defects inspecting apparatus is constructed with providing an illumination optical system, comprising: a light source for emitting a UV light, a laser light, or a UV laser light, etc.; a light-amount adjustment optical system for adjusting an light-amount of the UV light, the laser light, or the UV laser light; a slit-like light flux optical system for forming the UV light, the laser light, or the UV laser light into a slit-like light flux for fitting to a light receiving portion, such as a TDI image sensor, or the like; and a coherence reduction optical system for lowering coherency of the UV light, the laser light, or the UV laser light, emitting from the slit-like light flux optical system, and further being provided with a detection optical system, having an image sensor for detecting a detected image signal by picking up an image of reflection light from the sample irradiated by the illumination optical system, and an image processing portion for detecting the defects on the patterns formed on the sample upon the basis of information relating to the image signal of the sample detected by the detection optical system.

Also, according to the present invention, in the pattern defects inspecting apparatus mentioned above, it is characterized that as an image sensor of the detection optical system is applied an image sensor of time delay integrated (TDI) type having a sensitivity to the UV light.

And also, it is characterized that the image sensor of the time delay integrated (TDI) type is an anti-blooming TDI sensor, a surface irradiation type TDI sensor, in which an organic thin-film coating is treated on a cover glass thereof, or a reverse surface irradiation type TDI sensor.

Also, according to the present invention, there is provided a method for inspecting defects on pattern formed on a sample, comprising the following steps of: irradiating the UV laser light lowered in coherency thereof upon surface of a sample; obtaining an image signal by picking up an image of the surface of the sample irradiated by the UV laser light; detecting defects on the sample, being equal or less than 10 nm in size, by processing the image signal; and outputting information relating to position on the sample with respect to the detected defects being equal or less than 100 nm in size.

Further, according to the present invention, there is provided a method for inspecting defects, comprising the following steps of: irradiating the UV laser light lowered in coherency thereof upon a wafer having a diameter of 200 mm; detecting an image of the wafer by picking up an image of the wafer irradiated with the UV laser light; and detecting defects on patterns formed on the wafer, being equal or less than 100 nm, by processing the detected image of the wafer at throughput of equal or greater than three (3) pieces per an hour.

And also, according to the present invention, in the method for inspecting pattern defects, on the sample are formed with patterns having repetitiveness.

Those and other objects, features and advantages of the present invention will be apparent from the following more particular description of preferred embodiments of the invention, as illustrated in the accompanying drawings.

DESCRIPTION OF THE PREFERRED EMBODIMENTS

Figure 1:
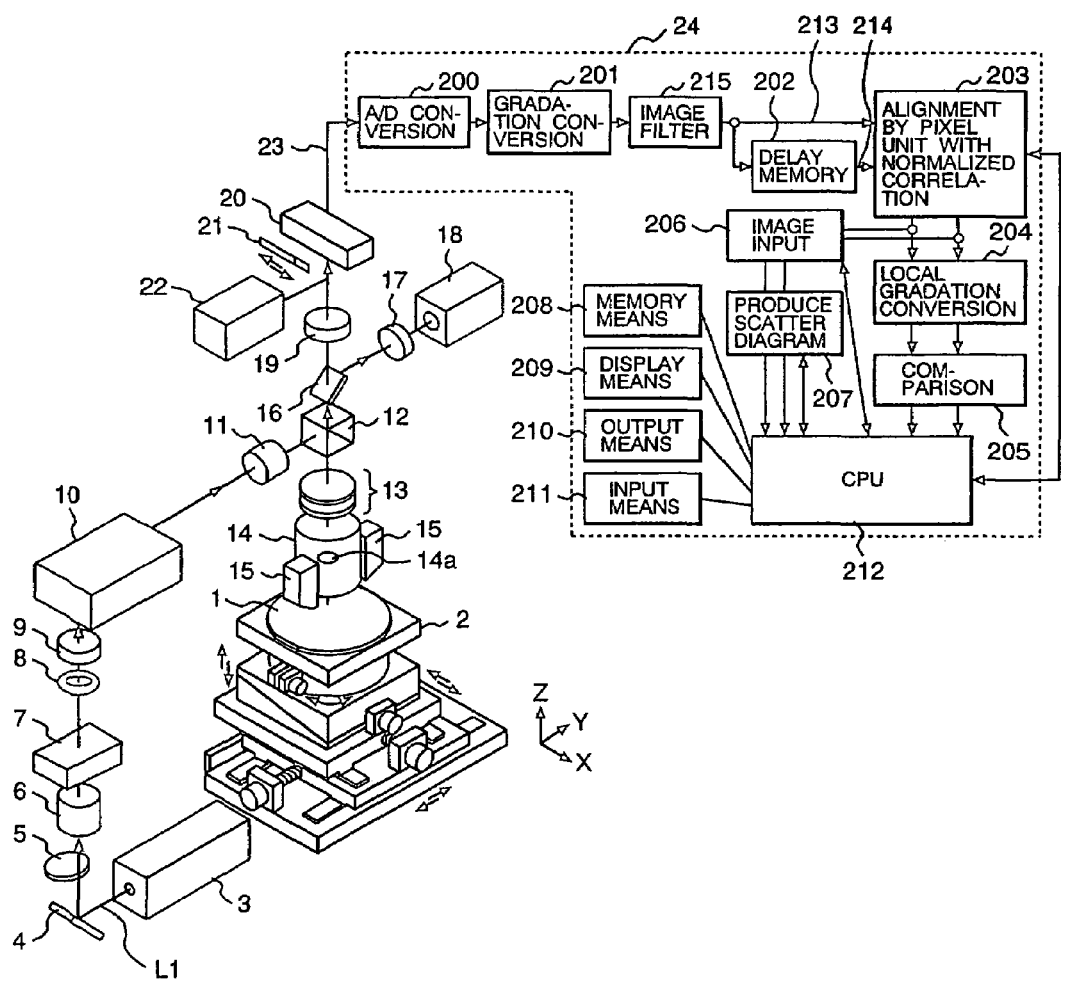
FIG. 1 is a view for showing the structure of an apparatus for inspecting pattern defects on patterns to be inspected, according to an embodiment of the present invention.

Hereinafter, embodiments, i.e., a method and an apparatus for inspecting defects on patterns to be tested, according to the present invention will be fully explained by referring to the attached drawings. FIG. 1 is a view for showing an embodiment of the apparatus according to the present invention. A stage 2 is built up with X, Y, Z and θ (rotation) stages, and this stage 2 is mounted a pattern to be tested or examined, such as, a semiconductor wafer (sample) 1, for an example. An illumination light source 3 is built up with, such as, a UV laser beam source irradiating the laser beam having wavelength of 266 nm or 355 nm therefrom, i.e., it is a light source for illumination of a sample 1. As such the UV laser beam source, it may be built up with a device of generating a third high-harmonic (355 nm) or a fourth high-harmonic (266 nm) of a basic wavelength, in which a laser beam from a solid YAG laser is converted in the wavelength thereof through a non-linear optical crystal, etc. Or, it may be possible to adopt a laser beam source having the wavelength of 193 nm, or 248 nm. If being available as such the UV laser beam source, it is also possible to adopt one having wavelength of 100 nm or less than that, thereby improving the resolution much more. Further, it does not matter if the laser is in continuous oscillation or in pulse oscillation in the oscillation mode thereof, however in relation with a fact that an image is detected from an object 1 to be tested while driving the stage continuously, the continuous oscillation is preferable.

A light flux L1 from the laser beam source 3 is reflected upon a mirror 4, which is rotated around an optical axis at a desired position, and is limited or restricted in an amount, down to that necessary for inspection, by means of a ND filter (an adjustment optical system for light amount) 5 for restricting the amount of lights. The UV laser light is expanded to a certain size of light flux by means of a beam expander 6.

An optical system for exchanging optical illumination light path (an optical system for exchanging illumination area) 7 is used for setting the area of illumination upon the sample 1, exchanging between when inspecting and when adjusting an inclination. Thus, the optical system for exchanging optical illumination light path (the optical system for exchanging illumination area) 7 exchanges the illumination area, so that an illumination is made on a rectangle area or region (i.e., a slit-like area) 71 covering an image sensor 51 when inspecting, while it is made all over a detection area of a detector 18 when adjusting the inclination. However, when inspecting, in the optical system 7 for exchanging optical illumination light path, an aperture diaphragm 8 is set at a conjugate point with a pupil 14a of an objective lens 14, thereby functioning to restrict the NA incident upon the pupil 14a. Through a lens 9, the laser beam is guided to an optical system 10 for lowering coherence.

The coherence lowering optical system 10 is provided for lowering the coherence of the laser beam emitted from the illumination light source 3. This coherence lowering optical system 10 may be a one, which can lower the time or the spatial coherence. As such the coherence lowering optical system 10, for example, it may be built up with a mechanism for scanning the laser beam from the illumination light source 3 on the pupil of the objective lens 14. An image of the laser beam from the coherence lowering optical system 10 is formed on the pupil 14a of the objective lens 14 through a lens 11.

A beam splitter 12 may be constructed with a polarization beam splitter in a case, and is constructed, so that the UV illumination light from the UV illumination light source 3 reflects thereupon, to be given upon the sample 1 through the objective lens 14, thereby giving a bright-field illumination thereupon, for example. When the beam splitter 14 is constructed with the polarization beam splitter, it has a function of reflecting the UV laser beam thereupon if the polarization direction of the UV laser beam is in parallel with the reflection surface, while passing it therethrough if the polarization direction is perpendicular to the reflection surface. Accordingly, since the UV laser beam is inherently a polarized light, it is possible to bring about total reflection of the UV laser beam, by means of the polarization beam splitter 14.

A group 13 of polarization elements has a function of adjusting a ratio pf polarizing of the illumination light arbitrarily, through controlling the polarization directions of the UV laser illumination light and the reflection light, so that the reflection light will not reach to an image sensor 20 with accompanying a blur or unevenness in brightness, due to the shape of pattern and/or the difference in density, and it may be constructed with a ½ wavelength plate and a ¼ wavelength plate, for example.

And, a beam splitter 16 and a lens 17, as well as, the detector 20, which are provided in the optical path defined between the beam splitter 12 and the image sensor 20, are so constructed, that an image with a wide visual field can be obtained by means thereof. Thus, when adjusting the inclination of the sample, the wide field image of the sample 1 is formed on the detector 18 by means of the lens 17, for enabling observation (picking-up of pictures) of the wide field image thereof.

Also, by means of an image-forming lens 19 is formed an image of the reflection light on the image sensor 20, which is detected by the objective lens 14. Insertion of a mirror 21, which can be inserted, on the optical path between the image-forming lens 19 and the image sensor 20 enables an image-forming of the sample 1 on the detector 22, being same to that formed on the image sensor 20.

In this manner, by setting a rotation angle of the ½ wavelength plate and the ¼ wavelength plate, respectively, with rotating them around the optical axes thereof, upon the basis of the spatial image formed on the pupil surface, which is detected from the detector 18, a CPU (not shown in the figure) controls the polarization condition of the reflection light generated from the circuit patterns formed on a semiconductor wafer 1, i.e., the diffraction light in the reflection light; therefore, it is possible to detect the image, for example, with reducing the diffraction light of $0^{th}$ order but hardly reducing diffraction lights of other higher orders, by means of the image sensor 20. As a result, the image of the patterns can be improved progressively in the contrast, and thereby stable detection sensitivity can be obtained. However, for the purpose of observation (picking-up of the pictures) of the spatial image on the pupil surface 14a of the objective lens 14 by means of the detector 18, it is necessary to replace the lens 17 with a lens or the like, which can form the spatial image on the pupil 14a on the detector 18.

As the objective lens 14, because of adoption of the UV light or the DUV light therein, it is possible to lessen an ill influence due to chromatic aberration by using a reflection objective lens. Also, when irradiating the UV light upon the sample, as the objective lens 14 is used one having the NA greater than 0.75.

The image sensor 20 has pixels, each being from 0.05 μm to 0.3 μm in the size, converted onto the sample, and providing an output of an image signal of density (or gradation) depending upon the brightness (gradation) of the reflection light from the semiconductor wafer 1, as one example of the patterns to be inspected. However, those optical systems are expanded on an optical frame or base not shown in the figure, and are constructed with the laser and the illumination optical system, the detection optical system, and the sensors, in one body. The optical base is provided on an upper portion of the stage 2, but in the manner not shown in the figure. For this reason, it is impossible to obtain a stable detection thereof, in particular with respect to change in temperature, and disturbance due to vibration, etc.

With such the structure mentioned above, the UV light (for example, the UV laser beam) L1 emitted from the illumination light source 3, being reflected upon the mirror 4 and penetrating through the ND filter 5 for limiting the light amount, is expanded by the beam expander 6, to be incident upon the objective lens 14 through the coherence reducing optical system 10, the lens 11, the beam splitter 12 and the group 13 of polarization elements, thereby being irradiated upon the sample (i.e., the semiconductor wafer) 1. Namely, after being converged in the vicinity of the pupil of the objective lens 14 by means of the lens 11, the UV light L1 is given upon the sample 1 as the Koehler illumination. The reflection light from the sample 1 is detected by the image sensor 20, after passing through the objective lens 13, the group 13 of polarization elements, the beam splitter 12, and the image-forming lens 19, sequentially from the above of the sample 1 in the vertical direction.

When being inspected, the sample 1 is always detected on the surface to be tested, i.e., the position in the Z direction thereof, in a focus detector system 15, through a method not shown in the figure, while moving the semiconductor wafer 1, as an example of the pattern to be tested, at a constant speed with scanning the stage 2, thereby controlling the stage 2 in the Z direction so that the distance between the objective lens is constant. The image sensor 20 detects brightness information (i.e., gradation image signal) of the pattern to be tested, which is formed on the semiconductor wafer 1.

A signal processor circuit 24 is constructed with an A/D converter 200, a gradation conversion portion 201, a video filter 215, a delay memory 202, an position alignment portion 203, a local gradation conversion portion 204, a comparing portion 205, a CPU 212, an image input portion 206, a scatter diagram producing portion 207, a memory means 208, a display means 209, an output means 210, and an input means 211, etc.

The A/D conversion portion 200 converts gradation image signal, which can be obtained from the image sensor 20, into digital video signal, thereby providing an output of video signal of the sample. For example, ten (10) bits data is adopted. The gradation converter 201 performs such the gradation conversion described in Japanese Patent Laying-Open Hei 8-320294 (1996) upon the 10 bits digital video signal, which is outputted from the A/D converter 200. Thus, the gradation converter 201 treats it with the logarithm transformation, the exponential transformation, or the multinomial transformation, etc., thereby compensating the image, and it is so constructed that it can provide an output of eight (8) bits digital signal, for example.

The video filter 215 is a filter provided for removing noises being characteristic to the image detected under the UV light from the image, which is gradation-converted and compensated, with high efficiency. The delay memory 202 is a memory portion for memorizing a reference image signal therein, and it memorizes the output image signal from the video filter 215, for a one cell or a plural number of cells, or for an one tip or a plural number of tips, being repetitively formed on the semiconductor wafer, so as to delay. Herein, the cell constitutes a unit of repetition within the tip. However, the video filter 215 may be provided after passing the delay memory 202. The position alignment portion 203 is a portion for detecting an amount of positional shift or deviation between the image signal (i.e., the detected image signal obtained from the sample) 213 treated with the gradation conversion, which is outputted from the gradation converter 201, and the delayed image signal (i.e., the reference image signal) 214 obtained from the delay memory 202, through the normal function, thereby aligning the position by a unit of the cell. The local gradation conversion portion 204 is a portion for conducting the gradation-conversion upon both or one of the image signals, being different in the characteristic quantity (i.e., the brightness (the difference in tone), the contrast, the differential value, the standard deviation, the texture, etc.) of a normal portion, locally (i.e., for each predetermined area or region), so that the characteristic quantity of the said normal portion coincides with each other locally (i.e., for each predetermined area or region). Thus, both or one of the image signals are compensated through the local gradation-conversion, so that the characteristic quantity of the detected image signal and that of the reference image signal are coincident with each other, with the normal portion. With doing this, if a difference is generated between the detected image signal and the reference image signal, in the brightness, the contrast or the like, it is possible to bring them to be coincident with, through the local gradation-conversion, and therefore, without generating erroneous information, it is possible to detect the defects with high sensitivity, by means of a decision threshold value upon basis of the difference in the characteristic quantity thereof.

The comparison portion 205 is a portion for comparing the detected image signals by themselves, which are treated with the gradation-conversion in the local gradation-conversion portion 204 locally (i.e., for each predetermined area or region), thereby detecting the defects or the defect candidates by means of the decision threshold value upon basis of the difference in the characteristic quantity. Thus, the comparison portion 205 compares the reference image signal, which is outputted from the delay memory 202 and is delayed by an amount corresponding to the cell pitch, etc., with the detected image signal.

By inputting the coordinate, such as alignment data or the like on the semiconductor wafer 1, through the input means 211, being constructed with, such as a keyboard, or a disc, etc., the CPU 212 produces defect inspection data upon the basis of the coordinate, such as the alignment data, etc., on the semiconductor wafer 1, and stores it into the memory means 208. This defect inspection data can be displayed on the display means 209, such as a display, if necessary, and also can be outputted to the output means 210. Further, the details of the comparison portion 205 may be such, as shown in Japanese Patent Laying-Open No. Sho 61-212708 (1986), for example, and may be constructed with a position alignment circuit for an image, a differential image detector circuit for the image aligned in position, an anti-coincidence detector circuit for digitizing the difference image, and a characteristic extractor circuit for calculating out an area, a length (a projection length), or the coordinate, etc., from the digitized output. In brief, from the comparison process portion 205 is outputted information in relating with the position and the sizes of the defects on the pattern to the CPU 212, therefore the defect inspection data is produced in the CPU 212.

The image input portion 206 is a portion for inputting in synchronism or in non-synchronism, for the purpose of producing scattered diagrams for both images, which are aligned in the position by a unit of the cell in the position alignment portion 203. The scattered diagram producing portion 207 is provided for producing the scattered diagrams, between the characteristic quantity of the detected image by a unit of pixel and the characteristic quantity of the reference image by a unit of pixel, for respective categories (i.e., the brightness (the difference in tone), the contrast, the differential value, the standard deviation, the texture), for each the predetermined area (locally), with respect to the both images inputted in the image input portion 206, thereby for displaying them on the display means 209, for example.

Figure 26:
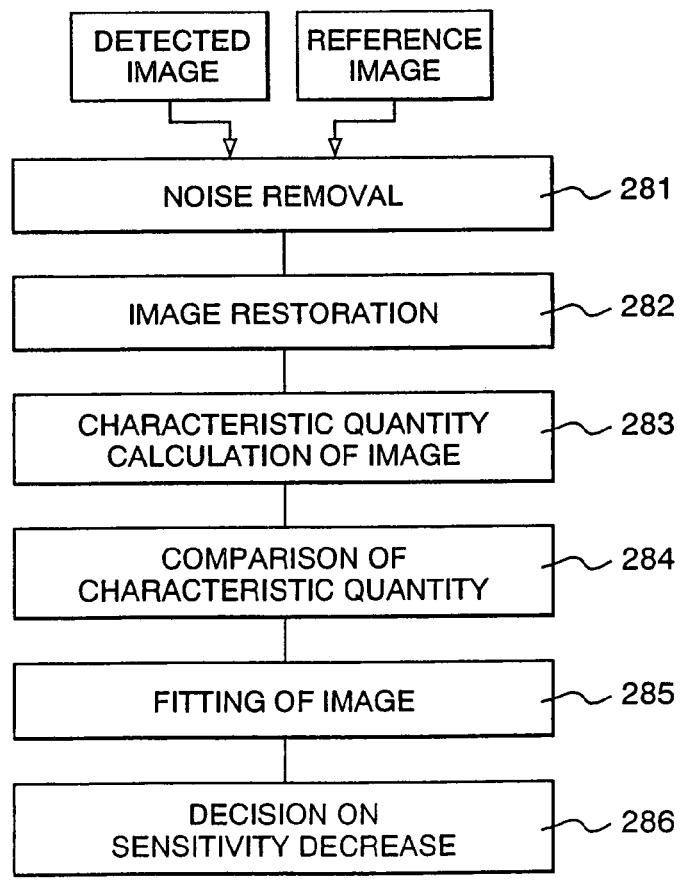
FIG. 26 is a view for explanation about an image filter in the image processing, according to the present invention.
Figure 27:
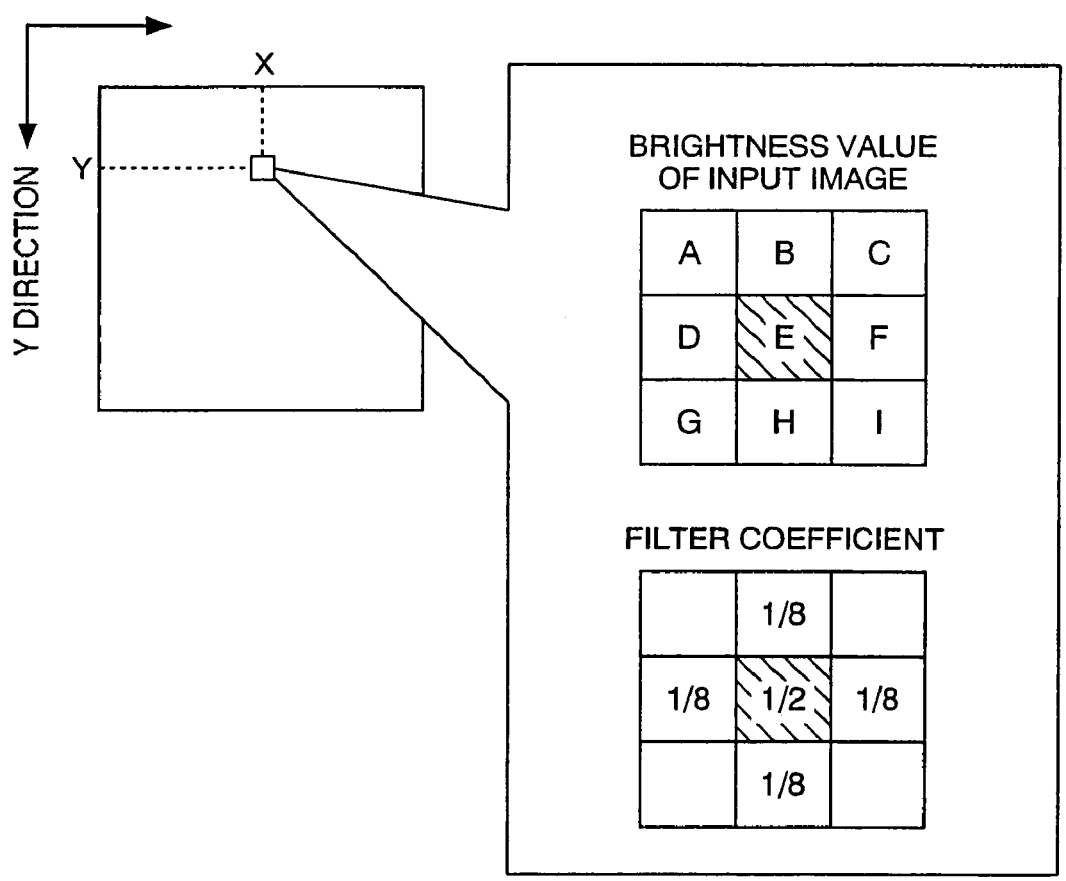
FIG. 27 is a view for explanation about the image filter in the image processing, according to the present invention.

An example of the video filter 215 will be explained. FIG. 26 shows a flow of processes. First, upon the detected image and the reference image inputted are conducted removal of noises (281) and improvement on image quality (282), depending on the necessity thereof, thereby improving the S/N ratio. For the removal of noises, various kinds of filters are prepared; therefore it is possible to select it depending upon the target and/or the quality of noises. As an example thereof, a method can be listed up, in which values in the vicinity thereof are used with weight. In actual, the values in the vicinity of n×m, with respect to the pixel on which attention is paid, are multiplied with a filter coefficient(s) to be added with. In FIG. 27, it is the case where m=n=3, and the weight of each the pixel value in the vicinity is one-eighth (⅛). The value of the attended pixel comes to be (Eq. 1).

$$F(i,j)=B\cdot 1/8+D\cdot 1/8+F\cdot 1/8+H\cdot 1/8+E\cdot 1/8 \quad \text{(Eq. 1)}$$

The size and the coefficient of the filter can be changed flexibly, by using a lookup table thereof. As another example, there is known a median filter. With this, taking a central value among the brightness values in the vicinity where the setting is made, it is possible to remove an ill influence of a singular point. Alternatively, in other example is used the Gaussian function. With this, smoothing of image is conducted through the convolution; i.e., first convoluting an average 0 upon the image f(x,y), and then two (2)-dimensional Gaussian function (Eq. 2) upon (Eq. 3).

$$G(x,y)=(1/2\pi\sigma^2)\cdot \exp(-(x^2+y^2)/2\sigma^2) \quad \text{(Eq. 2)}$$

$$F(x,y)=G(x,y)\otimes f(x,y)=\int\int G(x+u,y+v)\cdot f(x,y)dudv \quad \text{(Eq. 3)}$$

where, ⊗ means the convolution.

Also, in other example, it is possible to remove the noises generating irregularly, by using the Fourier transform.

Next, restoration is made (282) on the image, which is deteriorated through the noise removal (281). As an example of this, the restoration is made by means of the Wiener filter. In this, the image is given, so that an averaged square error between the image f(x,y) after being inputted and the image f'(x,y) after the restoration comes to the minimal.

Further, it is checked whether there is a large difference or not, in a view between the detected image and the reference image to be compared with. Indexes for evaluation include the characteristic quantity (i.e., the brightness (tone value), the contrast (the brightness value), the dispersion of brightness (the standard deviation), the frequencies of noise components, the texture). Then, upon the detected image and the reference image, which are aligned in the position by a unit of pixel, the characteristic quantities are calculated out (283) for the respective categories; i.e., the brightness (tone value), the contrast, the dispersion of brightness (the standard deviation), the frequencies of noise components, the texture, etc., for each the predetermined area corresponding thereto (for each location) In the normal portion, if there is local difference between the detected image and the reference image in any one of the characteristic quantities, then first of all, sequential image compensation (i.e., sequential gradation-conversion) is conducted, locally, so that those characteristic quantities come close to each other. Thus, for each category, the characteristic quantities (such as, the tone value, or the brightness value, etc.) of the detected image and the reference image are compared with, for each area corresponding thereto, thereby extracting the difference therebetween. For example, for each category, and for each area, the scattered diagram is produced, by depicting the brightness value, as the characteristic quantity of the detected image by a unit of pixel of, on the horizontal axis, while the brightness value of the reference image, as the characteristic quantity by a unit of pixel, on the vertical axis. Then, compensation coefficients (a,b) are obtained upon the basis of an intersection point b between an inclination a of a line drawn in the area mentioned above, by fitting the straight line thereto (i.e., a linear approximation), for example, on the scattered diagram that is produced for each area. And, for example, compensating one of the images, i.e., the detected image f(x,y) (i.e., fitting of the image) (285) through the compensation coefficient mentioned above, for each area, enables to obtain the detected image signal f'(x,y), being coincident with the reference image in the characteristic quantity thereof, for each area, if it is the normal portion. Namely, as a result of the compensation, the detected image and the reference image are scattered under the condition that they are restricted onto a straight line of 45 degree in the scattered diagram, and thereby setting a decision threshold value for deciding to be the defects or the defect candidates, with respect to the difference (the difference image) between the detected image and the reference image, by a straight line having a certain width to that of 45 degree. In this manner, the decision threshold value can be obtained from the scattered diagram.

$$f'(x,y)=a\cdot f(x,y)+b$$

In this fitting of image, the Wiener filter mentioned above may be applied between the detected image and the reference image. Also, in video processing, if the image is at a level where the fitting of the local characteristic quantity is impossible, the sensitivity is lowered down, by increasing the decision threshold value in the comparison process portion 205, for extracting the defects and the defect candidates with respect to the difference (the difference image) between the detected image and the reference image, thereby suppressing generation of the erroneous information (286).

Further, the method for calculating the defects in the video processing portion 24 can be realized, in the details thereof, by that shown in Japanese Patent Laying-Open No. 2000-194323, for example.

Next, explanation will be given on the illumination light source 3. Although shortening is necessary, in particular, in the wavelength thereof, for achieving the high resolution, it is thought appropriate to use the laser for the light source, as a means for obtaining an illumination of high luminance within wavelength region of the UV, being most effective in the effect thereof. As was mentioned in the above, adopting the UV laser light as the light source brings about a large merit. According to the present invention, there is shown a method of using the illumination by means of the UV laser light.

Figure 2A:
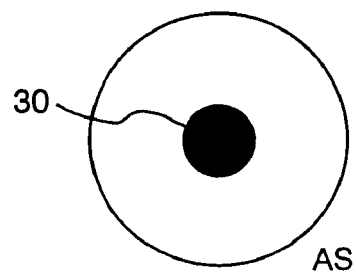
FIGS. 2(a) and 2(b) are views for showing illumination conditions on a pupil and a visual field of an objective lens for detection, under the illumination by means of a discharge tube.
Figure 2B:
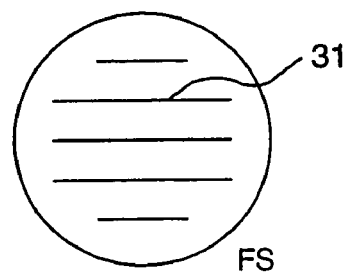
Figure 3A:
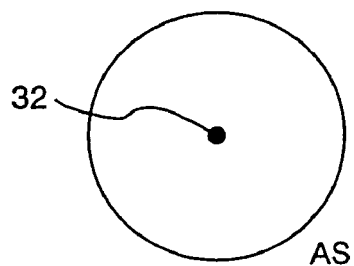
FIGS. 3(a) to 3(d) are views for showing illumination conditions on a pupil and a visual field of an objective lens for detection, a pattern on the visual field and a signal detected therefrom, but under the illumination by means of laser radiation.
Figure 3B:
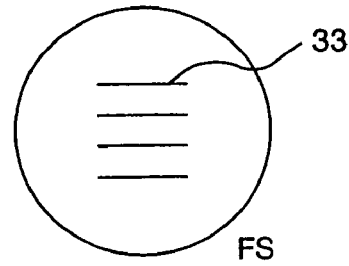
Figure 3C:
Figure 3D:
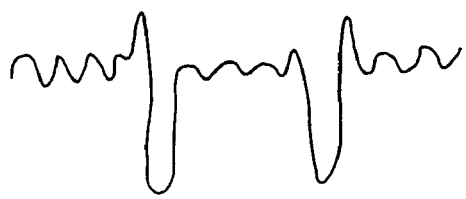

FIGS. 2(a) and 2(b) show the condition of illumination on the pupil of the objective lens and a visual field, when being illuminated under an ordinary white light. AS in FIG. 2(a) indicates the pupil, and FS the visual field. At the position of the pupil AS, an image 30 of the light source is formed, while the entire of a visual field 31 is illuminated, equally, at the position of the visual field FS.

Next, in FIGS. 3 (a) to 3(d) are shown the cases where the illumination is obtained by means of the UV laser light source. In this case, as shown in FIG. 3(a), the light source image 32 comes to be a point at the position of the pupil AS. The illuminated circuit pattern shown by 30 on the visual field FS, as shown in FIG. 3(b), if being the pattern in the cross-section thereof as shown in FIG. 3(c), comes to be an image having a detection waveform shown in FIG. 3(d). In this manner, when obtaining the image of circuit pattern while illuminating it by the laser light, an overshoot or an undershoot, or a speckle occurs at the edge portion thereof. The reason thereof lies in a fact that σ of the illumination is small. In other words, the illumination onto the visual field FS under the objective lens 14 is not carried out from various angles.

Figure 4A:
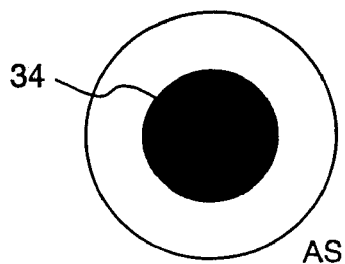
FIGS. 4(a) and 4(b) are views for showing illumination conditions on a pupil and a visual field of an objective lens for detection, under the illumination by means of laser radiation, being widened or spread on the pupil thereof.
Figure 4B:
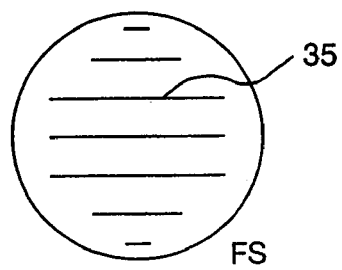

Under the illumination of an ordinary white light, an illumination is performed to have a certain size on the pupil AS, thereby illuminating to the visual field FS from the directions having an angle range corresponding to the NA (i.e., the number of aperture) of the objective lens 14. Under the coherent light (i.e., having coherency), such as, the laser light, σ (in proportion to the size of a light source on the pupil) comes to be zero (0). This is because an image of the light source is a point with such the coherent light, therefore the image on the pupil becomes a point. Of course, as shown in FIG. 4(a), though it is possible to project the light flux 34 expanded by other lens system upon the pupil 14a (AS) of the objective lens 14, however since the UV laser light has the coherence, it comes to be the same result (see 35 shown in FIG. 4(b)) where all the lights come out from the position of σ=0, therefore it brings about no solution thereof.

Accordingly, there is a necessity of a means for lowering the coherence of the UV laser light. For the purpose of lowering the coherence, it is sufficient to reduce either one of the time coherence or the spatial coherence thereof.

Figure 5A:
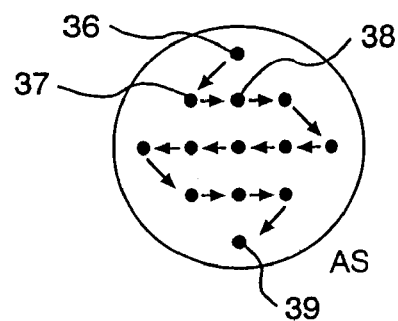
FIGS. 5(a) to 5(d) are views for showing illumination conditions on a pupil and a visual field of an objective lens for detection, under the illumination by means of laser radiation according to the present invention.
Figure 5B:
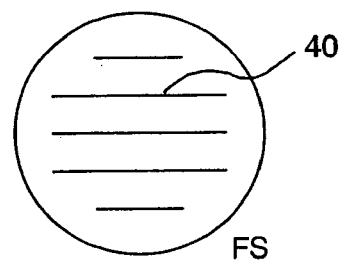
Figure 5C:
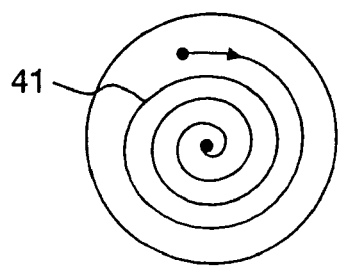
Figure 5D:
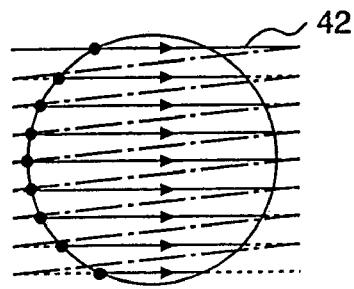

Then, according to the present invention, as a function of a light scanning mechanism (or a light scanning system) for scanning on the pupil, which constructs a light modulator as the coherence reducing optical system 10, it is proposed that illumination 40 is made upon the visual field shown in FIG. 5(b) by scanning, for example, first by illuminating upon the position 36 within the FIG. 5(a), and then upon the position 32, and the upon the position 33 . . . , while forming the image of light source upon the pupil 14a of the objective lens 14 in the inspecting apparatus. And, as shown in FIG. 5(c), the scanning 41 may be made in a swirl-like manner on the pupil 14a. Also, as shown in FIG. 5(d), the scanning 42 may be made in two (2)-dimensional manner. During this, images of the speckle, the overshoot and the undershoot may be obtained at the respective positions, however they have no coherence due to the difference in the time instance when each being obtained. Accordingly, adding those images upon the image sensor 20 enables obtaining the image being same to that formed with the incoherent light source. For achieving the addition thereupon, suitably, the image sensor 20 has a pixel size from about 0.05 μm to about 0.3 μm, being converted on the sample (on the visual field), and is a detector of accumulation or storage type (in more details, the TDI sensor), such as a CCD. Thus, such an image sensor of accumulation or storage type, it can be considered that a linear sensor is applied to.

Figure 6:
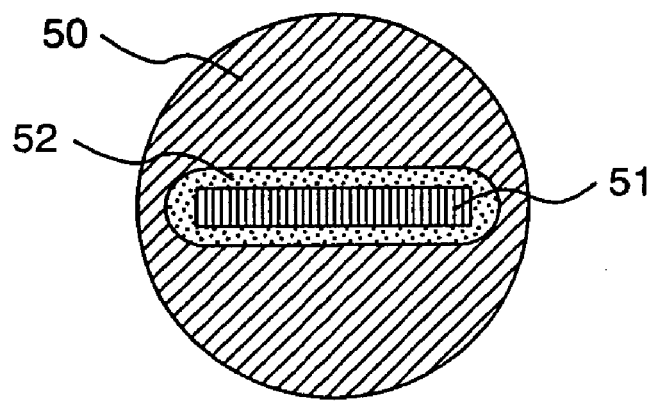
FIG. 6 is a view for showing a relationship between a CCD detector and an illumination area on the visual filed, according to the present invention.
Figure 7:
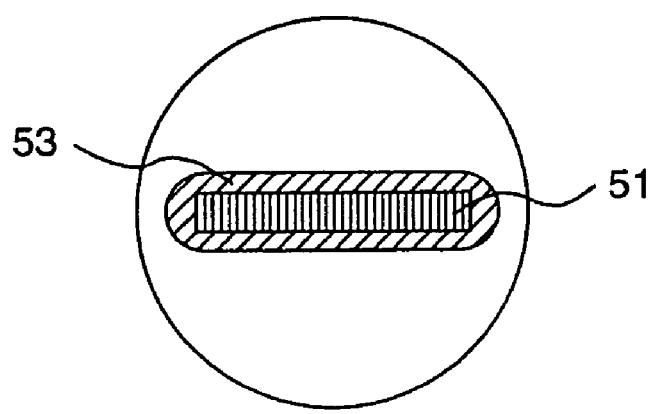
FIG. 7 is also a view for showing a relationship between a CCD detector and an illumination area on the visual filed, according to the present invention.

As shown in FIG. 6, if illumination is made all over surface of the visual field to the linear sensor 51, only the illumination at an area 52 can contribute to the detection, but an area 50 other than that has no contribution to the detection, which occupies a large part of an optical power. Then, for the purpose of improving the luminance, it is preferable to perform a line-like (or slit-like) illumination onto the linear sensor 51 within the area 53, as shown in FIG. 7. According to the present invention, with such the image sensor 20, it is constructed by using a sensor of time delay integration type among the CCD sensors, i.e., the TDI (Time Delay Integration) type. In case of the TDI sensor, N stages (from several tens to 256 stages) of light receiving portions are aligned on the visual field in a shorter direction thereof, while a plural number of the stages are aligned in the longer direction, thereby building up the linear sensor.

Figure 8A:
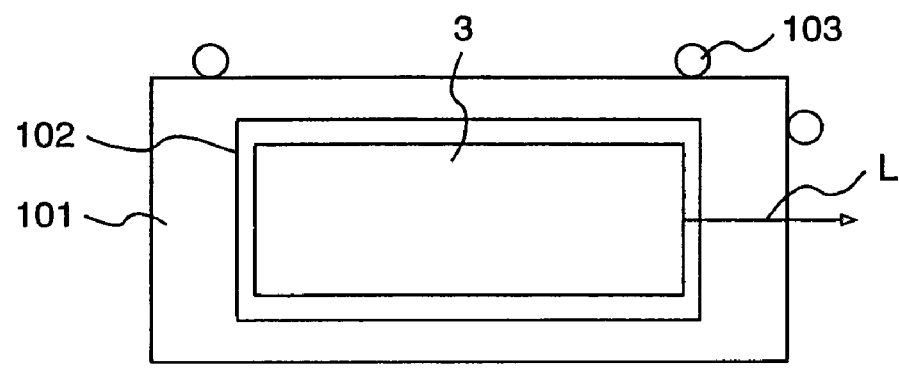
FIGS. 8(a) and 8(b) are views for showing a relationship in an attachment of a laser beam source, according to the present invention.
Figure 8B:
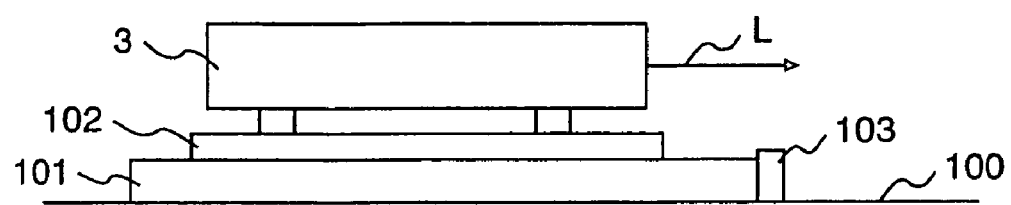

FIGS. 8(a) and 8(b) show the structure of the laser beam source. The laser beam source 3 is fixed on a plate 102. A plate 101 is fixed with aligning to an optical base 100. Position alignment is made, for example, by fixing with using a pin 103 fixed on the optical base 100 as a guide. Herein, it is assumed that the pin 103 is adjusted with respect to an optical axis of the optical system. The plate 102 is fixed on the plate 101. The laser beam source 3 happens to be replaced with new one, due to the lifetime of a laser oscillator. When the laser beam source 3 is replaced, there is a probability that the stoppage time of the apparatus comes to be long if adjusting the optical axis of the optical system. For this reason, preferably, the laser beam source 3 is completed in adjustment of the optical axis thereof before it is mounted for replacement, so as to obtain a desired performance at the lowest.

Figure 9A:
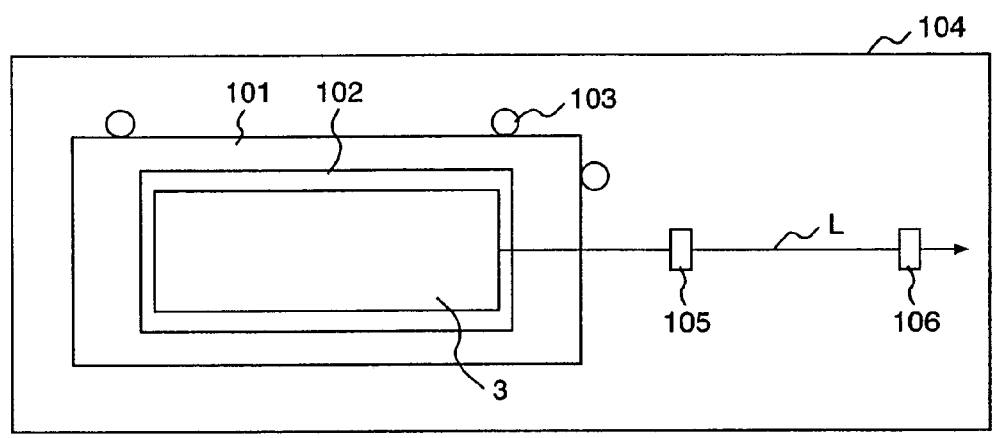
FIGS. 9(a) and 9(b) are views for showing a adjustment manner in the attachment of the laser beam source, according to the present invention.
Figure 9B:
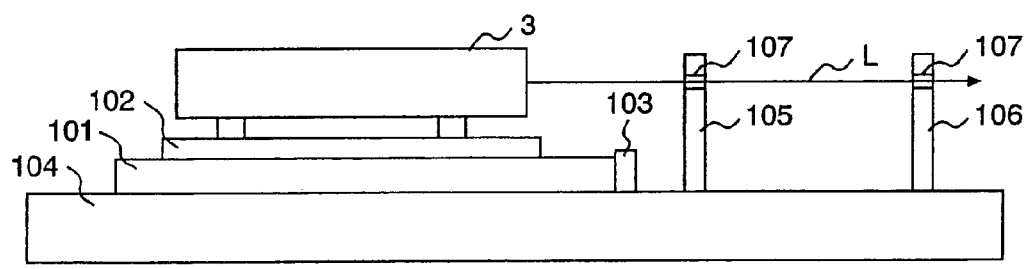

FIGS. 9(a) and 9(b) show an example of a jig for adjustment of optical axis. An optical axis adjustment base 104 is fixed by the pin 103 on the position being same to that of the optical base 100. Targets 105 and 106 are same in the height, and are fixed in parallel relationship with the position of the pin 103, while each being opened with a pinhole 107 for passing the laser beam therethrough. The distance between the targets 105 and 106 has a sufficient length for adjusting the laser beam source 3. In this structure, the plate 101 is fixed onto the optical adjustment base 104. The laser beam source 3 is provisionally fixed on the plate 102 in advance. Then, the plate 102 is mounted on the plate 101, thereby emitting the laser beam therefrom. The light flux L is adjusted in the right-hand and the left-hand side directions (i.e., in the horizontal direction) by means of the plate 102, so that it can pass through the pinholes 107 of the targets 105 and 106, while by the laser beam source 3 itself in the gate direction (i.e., in the vertical direction). After the adjustment, the plate 102 and the laser beam source 3 are fixed, and further the plate 102 is fixed onto the plate 101. In this manner, the light flux of the laser beam source 3 is adjusted upon the basis of the pin 103. Thereafter, replacing with the laser beam source 3 fixed on the plate 101 onto the optical base 100 brings about the coincidence of the optical axis thereof.

Figure 10:
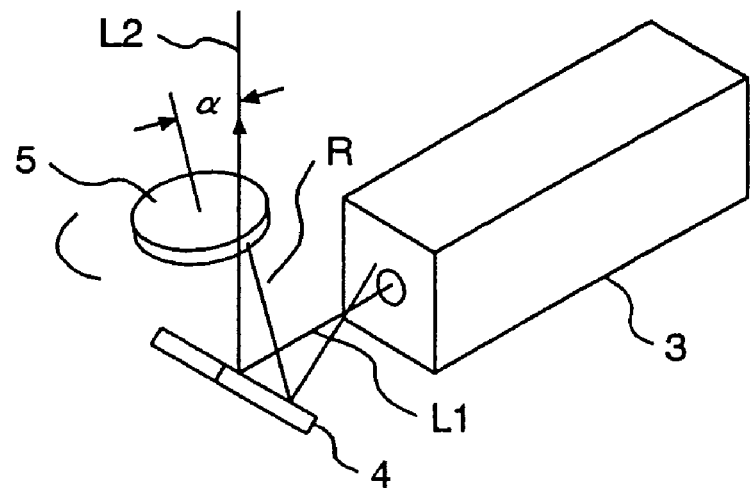
FIG. 10 is a view for showing a manner for adjusting an amount of lights, according to the present invention.
Figure 11:
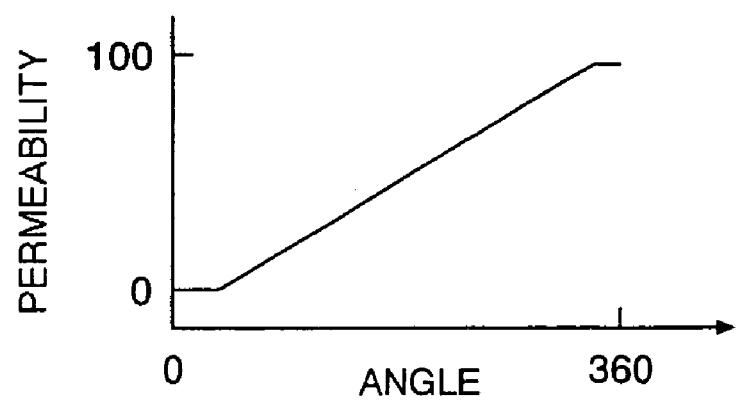
FIG. 11 is a view for showing a characteristic curve of an adjuster of light amount, according to the present invention.
Figure 12A:
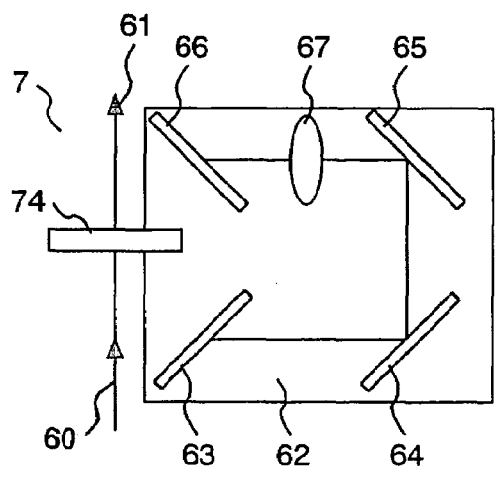
FIGS. 12(a) to 12(d) are views for explanation about an idea of exchanging the illumination area or region, according to the present invention.
Figure 12B:
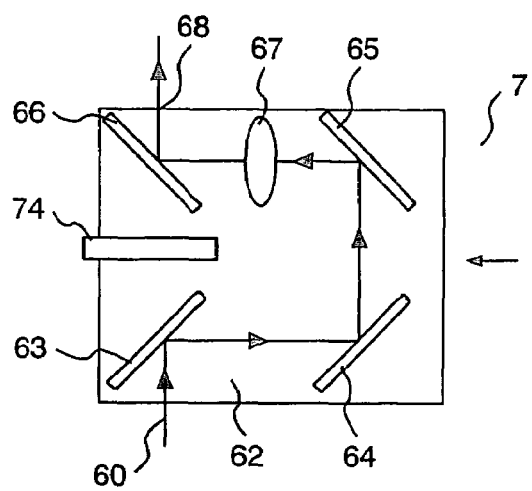
Figure 12C:
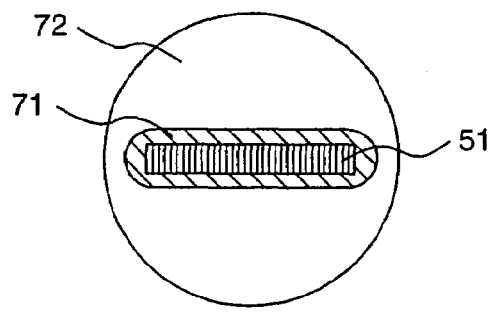
Figure 12D:
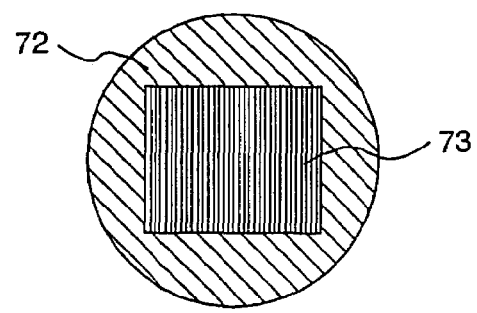

Next, explanation will be given on the ND filter (a light amount adjustment optical system) for restricting (adjusting) a light amount, by referring to FIG. 10. The light flux L1 from the laser beam source 3 is irradiated at the maximum output, for the stability of laser. For this reason, it is necessary to restrict the light amount reaching up to the image sensor 20. Thus, a ND filter 5 is inserted in the optical path. As such the ND filter 5 is used a filter changing the permeability depending upon the angle, as shown in FIG. 11, for example. The ND filter can be rotated through a method, but not shown in the figure; thus, includes a light amount adjustment system for fixing at a predetermined angle. Also, the ND filter 5 is inclined by an angle α to the light flux L2. It is sufficient that the angle α is set at such an angle that the light flux R reflected from the ND filter 5 will not directly turn back to a laser emission opening of the laser beam source 3. Namely, it is for the purpose of protection from a phenomenon, such as, interference occurs within the oscillator of the laser beam source 3, thereby bringing the laser output into an unstable condition. As was explained in the above, the light amount adjustment optical system is constructed with the ND filter 5, which is able to lower the light amount, and the optical amount setting system, which can set the penetrating light at an arbitrary amount by changing the inclination angle α in optical axis of the ND filter portion with respect to the optical axis L2.

Next, explanation will be given on the optical path exchanger system (i.e., illumination area exchanger means) 7. FIGS. 12(a) to 12(d) show the structure of the optical path exchanger system 7. Within the optical axis 60 is inserted a homogenizer (i.e., a slit-like light flux optical system) 74, for the purpose of illuminating the sample 1 by the slit-like light flux when inspecting. And, it is constructed with mirrors 63, 64, 65 and 66, and a lens 67, which are fixed on a base 62, for illuminating upon an entire detection area 72 of the detector when adjusting the inclination. The base 62 is constructed, being movable into the side of the optical path 60, but through a manner not shown in the figure, thereby being constructed to exchange the optical path when inspecting and when adjusting the inclination.

Figure 13:
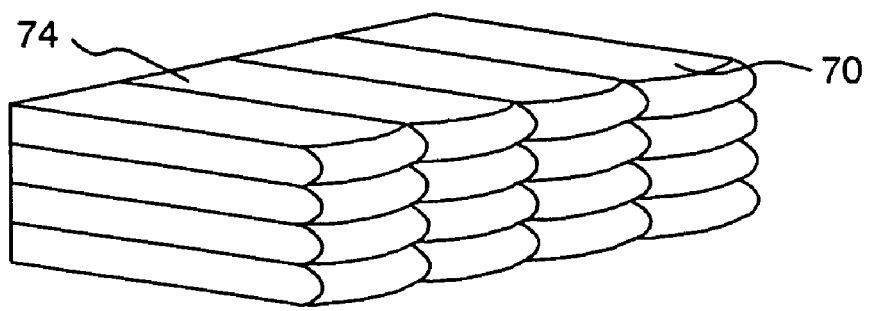
FIG. 13 is a view for explanation about an idea of forming the illumination area when inspecting, according to the present invention.

First, explanation will be given when inspecting. As was mentioned previously, because of use of the linear sensor, it is effective to perform a rectangular illumination 71 (i.e., illumination with using a slit-like light flux), irradiating all over the surface in the pixel direction while focusing or condensing onto the sizes of the sensor opening in the scanning direction, within the range of illumination when inspecting. For this reason, for forming a slit-like spot light (i.e., the light flux being focused or converged in the width direction of the linear sensor, such as the TDI sensor, etc.), the homogenizer 74 is inserted after emission of the light from the beam expander 6, as shown in FIG. 12(*a*), thereby achieving the rectangular illumination. FIG. 13 shows the structure of the homogenizer 74. The homogenizer (i.e., the slit-like light flux optical system) 74 is used, which is constructed by aligning a plural number of rectangular lens arrays 70 in the vertical and the horizontal directions. Thus, the homogenizer 74 is constructed by aligning the rectangular lens arrays 70 which, as shown, have a rectangular cross-sectional configuration, being different in the pitch in the vertical direction and the horizontal direction. With this, on the surface of a sample can be obtained the rectangular illumination (by the slit-like light flux) 71 (53). FIG. 12(*a*) shows the arrangement when achieving the rectangular illumination. FIG. 12(*c*) shows a range of illumination upon the surface of the sample 1. Thus, the illumination can be obtained within the range 71 (53) covering the image sensor, in the visual field 72 of the objective lens 14. However, the homogenizer 74 forms a large number of points of imaginary light source to the laser beam that is expanded in the beam diameter. Accordingly, as shown in FIG. 5, the large number of the points of imaginary light source are scanned at the same time upon the pupil 14*a*, in two (2) dimensional manner, thereby lowering the coherency.

By the way, the sample 1 is shifted onto the stage 2 by a method not shown in the figure. The sample 1 must be positioned, so that the patterns formed on the sample 1 are correctly aligned or fitted to the inspection direction of the apparatus, i.e., the scanning direction, for reducing the detection errors. For that purpose, it is necessary to compensate an inclination of the sample 1. In the present embodiment, a method will be explained, in which the inclination compensation is carried out by using a detector 18, which is provided in the optical path. First, by using tips at both ends of the sample 1, alignment marks provided within the tips, but not shown in the figure, are detected, so as to calculate out the inclination of the sample 1. Since the inclination of the sample 1 is unknown, it is necessary to enlarge the detection range of the detector 18, by making the optic magnification smaller than that for use in the inspection. As was mentioned previously, since the illumination area for use in the inspection is rectangular, the target falls down into a condition where no illumination is made in the direction perpendicular to the scanning direction when it is detected by the detector of wide visual field. For this reason, it is necessary to make illumination all over the detection area of the detector.

Explanation will be given on the illumination when compensating the inclination. In FIG. 12(*b*) is shown the arrangement for achieving the illumination when compensating the inclination. The light flux 60 is bent by means of the mirrors 63, 64, 65 and 66. Since the light flux 68 comes to an ordinary illumination light flux, by the function of the lens 67 provided within the optical path, therefore the illumination area on the objective lens 14 is circle in the shape thereof. FIG. 12(*d*) shows illumination area on the surface of the sample 1. The illumination is made all over the surface within the visual view 72 of the objective lens 14, therefore it is possible to cover the detection area 73 of the detector 18, fully.

Figure 14A:
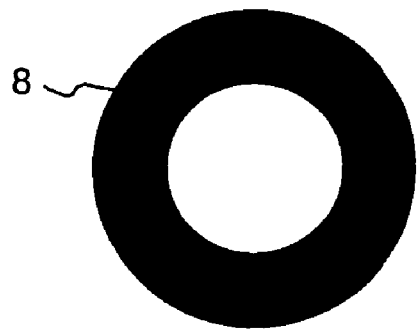
FIGS. 14(a) and 14(b) are views for explanation on an aperture diaphragm or stop, according to the present invention.
Figure 14B:
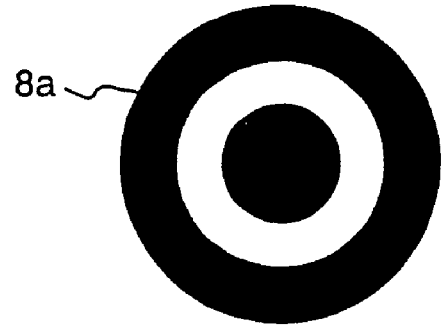

Next, explanation will be given on the aperture diaphragm system. FIG. 14(*a*) shows an example of the aperture diaphragm. The aperture diaphragm 8 is able to change a system, through which the light flux passes in the manner not shown in the figure. The position, at which the aperture diaphragm 8 is disposed, is that being conjugate to the pupil position of the objective lens 14. Depending on the surface shape of the sample as the target, it is possible to fit with the surface condition by the aperture diaphragm 8 being made changeable. Also, it is possible to make the aperture diaphragm 8 in a ring-like shape. FIG. 14(*b*) shows the shape of the aperture diaphragm 8*a* when achieving a ring illumination. Changing of the ring shape in various kinds by a manner, but not shown in the figure, enables the detection with higher resolution.

Figure 15:
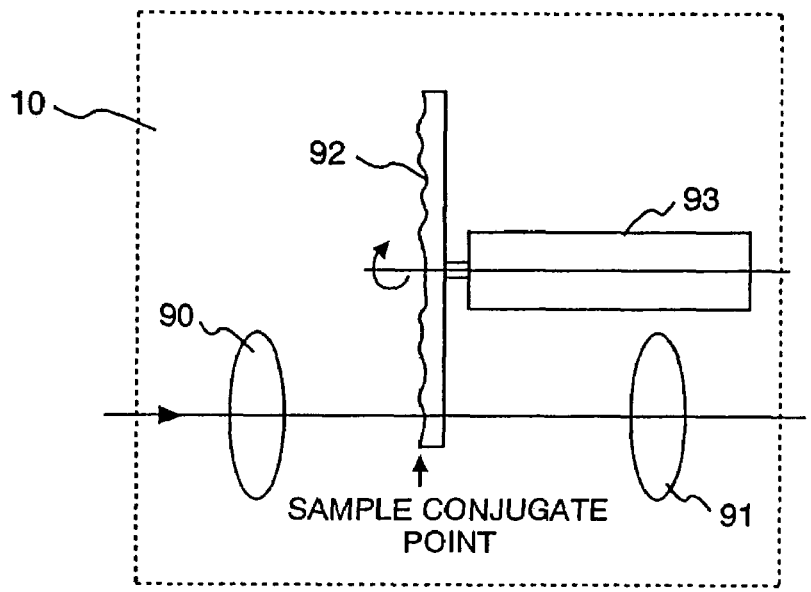
FIG. 15 is a view for explanation about an idea for lowering spatial coherence of the illumination by laser radiation, according to the present invention.
Figure 16A:
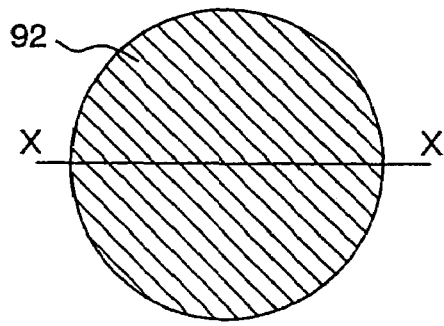
FIGS. 16(a) to 16(c) are also views for explanation about the idea for lowering spatial coherence of the illumination by laser radiation, according to the present invention.
Figure 16B:
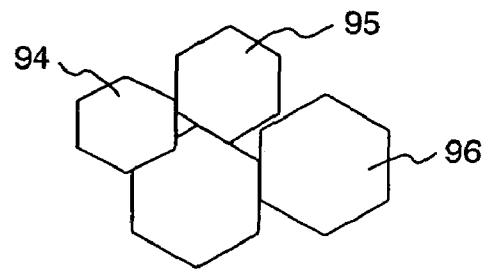
Figure 16C:
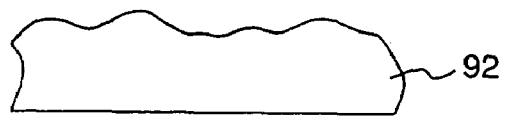
Figure 17:
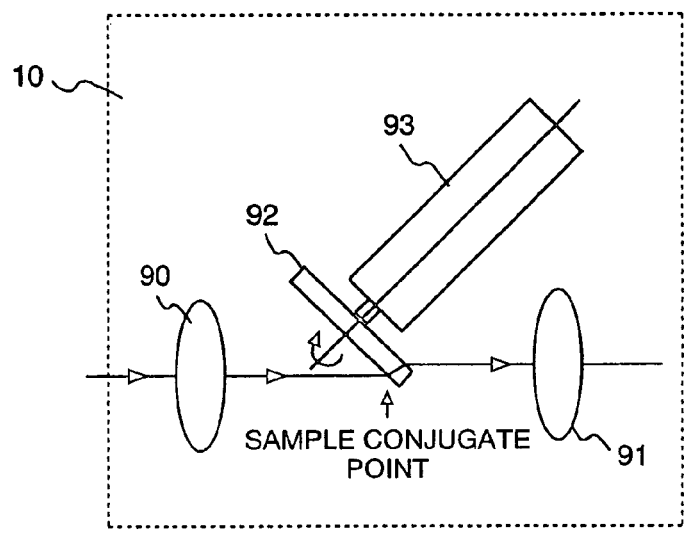
FIG. 17 is also a view for explanation about the idea for lowering spatial coherence of the illumination by laser radiation, according to the present invention.

Next, explanation will be given on the coherency reduction optical system 10. In the present embodiment, the reduction of coherency is achieved by a method of providing a diffuser panel within the laser optical path. FIG. 15 shows the structure of the coherency reduction optical system 10. An image of the UV laser beam is formed upon the pupil 14*a* of the objective lens 14 through the lenses 90 and 91. Within the optical path, a diffuser panel 92 is inserted, which moves crossing over the optical axis. The diffuser plate 92 can be rotated, for example, by means of a motor 93, so as to move crossing over the optical axis. The diffuser plate 92 is positioned in the vicinity of the conjugate point to the sample 1. The shape of the diffuser 92 is shown in FIGS. 16 (*a*) to 16(*c*). FIG. 16(*a*) shows the front view, and FIG. 16(*b*) a detailed view of the diffusion surface. FIG. 16(*c*) shows the cross-section X-X in FIG. 16(*a*). Observing from the surface, preferably, the diffuser 92 is formed by disposing or aligning particles 94, 95 and 96, each having a size of about 0.1 mm in the particle diameter and being formed in a polygon or a circle in shape. Also, the cross-section is preferable to random shapes depending on the particle diameter, even in an amount of concave and convex. Rotation of this diffuser plate 92 with high speed enables to negate the optical coherency completely. As a manner for rotating with high speed, applying an air turbine motor as the motor 93 enables the rotation speed of several kHz. As is shown in FIG. 15, there is a possibility the outer diameter of the motor 93 interferes with the lens 91, therefore the diffuser plate 92 must be made large. For this reason, a condition can be considered, where a desired rotation speed cannot be obtained, due to eccentricity, inertia, etc., when the diffuser plate rotates. In FIG. 17, there is shown an embodiment, in which the diffuser plate 92 has the size, being necessary and minimal. Introduction of the lenses 90 and 91 are same to those in FIG. 15 mentioned above. The diffuser plate 92 is disposed, inclining with an angle to the optical axis. The lens 91 was already positioned, by taking a gap in the optical axis due to the inclination into the consideration. With this, the interference between the motor 93 and the lens 93 can be prohibited, and therefore, the diffuser plate 92 can be manufactured to have the necessary and minimal outer diameter.

Figure 18A:
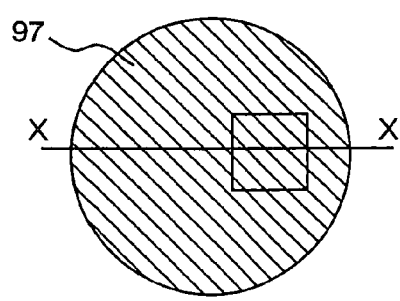
FIGS. 18(a) to 18 (c) are views for explanation about a second idea for lowering spatial coherence of the illumination by laser radiation, according to the present invention.
Figure 18B:
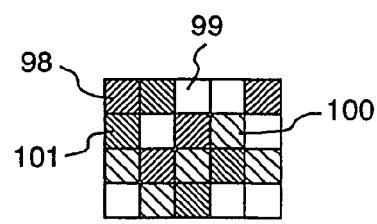
Figure 18C:
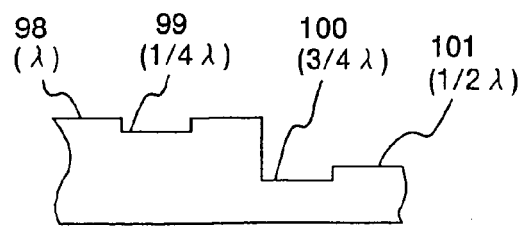

Also, similar effect can be obtained by provision of a rotational phase plate in the place of the diffuser plate 92 mentioned above. FIGS. 18(*a*) to 18(*c*) show the structure of the rotational phase plate. Thus, FIG. 18(*a*) is a view for showing the front view, FIG. 18(*b*) for sowing the details, and FIG. 18(*c*) a view for showing the cross-section X-X in FIG.

18(a). The rotational phase plate has such the thickness that no change occurs in phase at the position 98. For example, it is manufactured by shifting phase difference, ½λ, ¼λ and ¾λ . . . , in the step difference. A large number of those step differences, being different in depth, are treated thereon at random. This rotational phase plate is fixed onto the motor 92 in the place of the diffuser plate 92, as shown in FIG. 17, and rotation thereof enables to change the phase of the laser beam depending upon the depth of each of the steps, thereby the coherency of the laser can be lowered.

Figure 19:
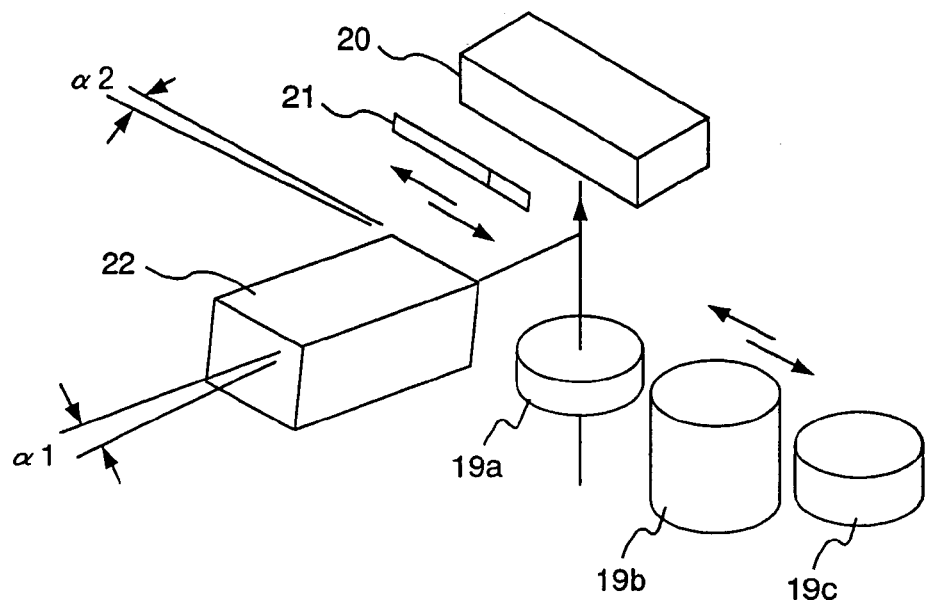
FIG. 19 is a view for explanation about an exchanging mechanism of an optical path in a detector, according to the present invention.

Next, the structure of the optical path exchanger mechanism will be shown. FIG. 19 shows the optical path exchanger mechanism. The optical path exchanger mechanism is provided for exchanging the optical path between the image sensor 20 and the detector 22. The mirror 21 can be inserted into the optical path by a manner, but not shown in the figure. The detector 22 is fixed at the position, being conjugate with the image-forming position of the image sensor 20, under the condition where the mirror 21 is inserted into the optical path. When inspecting, the mirror 21 is in a turnout or escaped condition, and it is shifted into the optical path when observing the inspection result, via a manner not shown in the figure, thereby enabling the observation of the sample 1 by means of the detector 22. And, the detector 22 is attached under the condition of inclining to the optical axis. The detector 22 is provided with a cover glass in a front thereof, in general, thereby protecting the sensor. The laser beams cause multi-interferences when being incident upon the surface and the reverse surface of the glass, therefore interference patterns appear on an observation screen in the detector. For this reason, the detector 22 is adjusted at angles α1 and α2, so that no interference occurs, to be fixed, thereby being able to protect from occurring the interference patterns thereon. Further, the detector 18 is also inclined in the same manner.

However, the image-formation lens 19 is used, by changing it to have the magnification corresponding to the pixel size. Thus, when the pixel size differs, not the objective lens 14, but the image-formation lens 19 is exchange. Further, the image-forming positions of the image-formation lenses 19a, 19b and 19c, having the respective magnifications, are set at the same position, irrespective of the difference in magnification thereof. Therefore, there is no necessity to change the position of the sensor 20 if the magnification is different, thereby enabling a stable detection. Also, the magnification is determined through the focal distance of the objective lens 14 and those of the image-formation lenses 19a, 19b and 19c, and the pixel size is determined by the size of aperture of the image sensor 20. However, due to errors occurring in manufacturing the objective lens 14 and the image-formation lenses 19a, 19b and 19c, as well as in install thereof, there is a probability that the magnification differs for each lot. Therefore, there will occur a problem that the detection sensitivity differs for each lot for the optical system, thus, for each apparatus. For this reason, each of those image-formation lenses 19a, 19b and 19c has a mechanism for making the focal distance thereof being variable.

Figure 20:
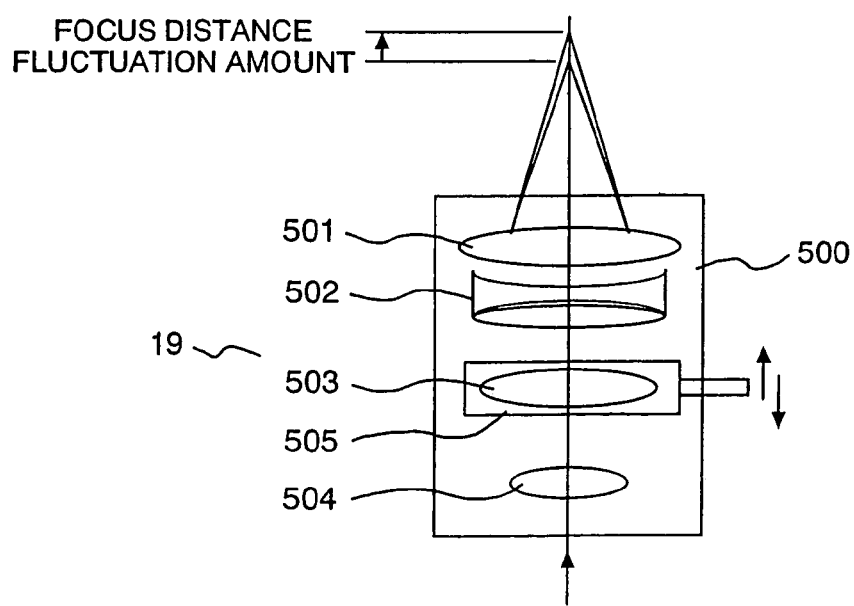
FIG. 20 is a view for explanation about the mechanism of a image-forming lens, according to the present invention.

FIG. 20 shows the cross-section view of the image-formation lens. The image-formation lens 19 is constructed by combining plural pieces of lenses 501, 502, 503 and 504 within a lens-barrel or -tube 500. The designing of those image-formation lenses are conducted, so that the focal distance thereof can be changed, for example, through shifting a one piece of those lenses into the optical thereof. In a case where the shifting of the lens 503, which is shown in FIG. 20, can change the focal distance, the lens holder 505 is so constructed that the lens 503 can be shifted from an outside of the lens barrel 500. Shifting this, with a manner not shown in the figure, causes a change in the focal position (or the focal distance), while the focal distance of the objective lens 14 is constant; therefore it is possible to cause a change in the magnification. Further, of course, a similar effect can be obtained by applying a zoom lens to the image-formation lens for making the magnification variable.

Figure 21:
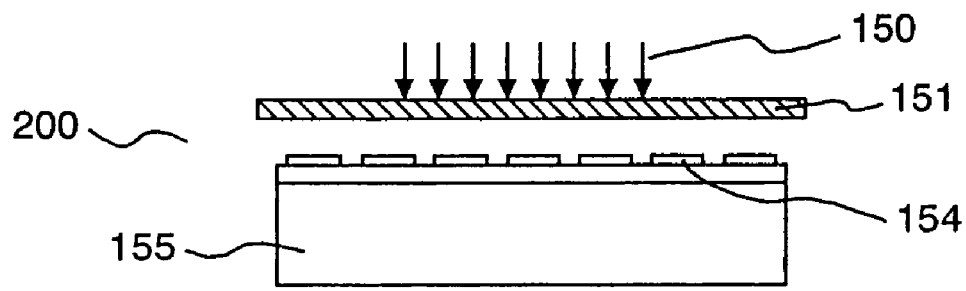
FIG. 21 is a view for explanation on a TDI image sensor, according to the present invention.

Next, explanation will be given on an example of the TDI sensor, being able to detect the UV light, in particular the DUV light in this manner. FIG. 21 shows a surface reflection type sensor. In case of using a DUV laser beam source as the illumination light source 3, it is necessary to apply an image sensor having sensitivity to the DUV light. In an image sensor 200 of surface irradiation type, incident light 150 enters into a CCD 155, penetrating through a cover glass 151 and passing through a gate 154, thereby being attenuated with the short wavelength; therefore it has almost no sensitivity to the wavelength less than 400 nm, and is unable to detect the DUV light effectively. Then, a method is already known, for detecting the DUV light by means of the image sensor having the sensitivity only to the visible lights, wherein an organic thin-film coating 152 is treated on the cover glass 151, so as to emit visible light responding to an incident DUV light thereupon.

Figure 22:
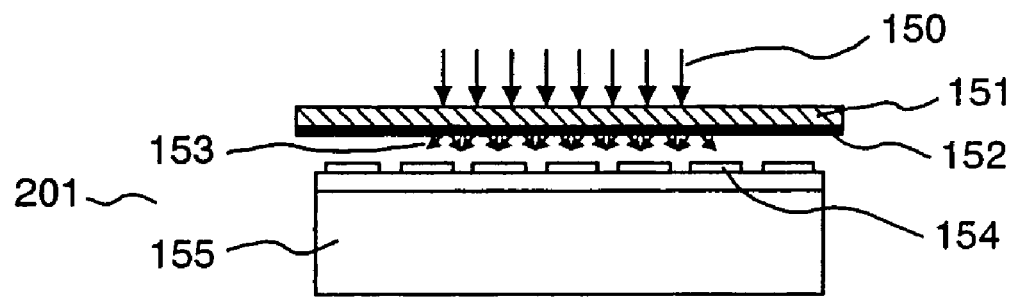
FIG. 22 is also a view for explanation on the TDI image sensor, according to the present invention.

FIG. 22 shows an image sensor of such organic thin-film coating type. In the organic thin-film coating type image sensor 201, the organic thin-film coating 152, receiving the penetrating light of the incident lights, emits fluorescence lights from the organic thin-film coating surface 152, therefore it can detect the DUV light by means of the surface irradiation type image sensor having the sensitivity to the visible lights.

Figure 23:
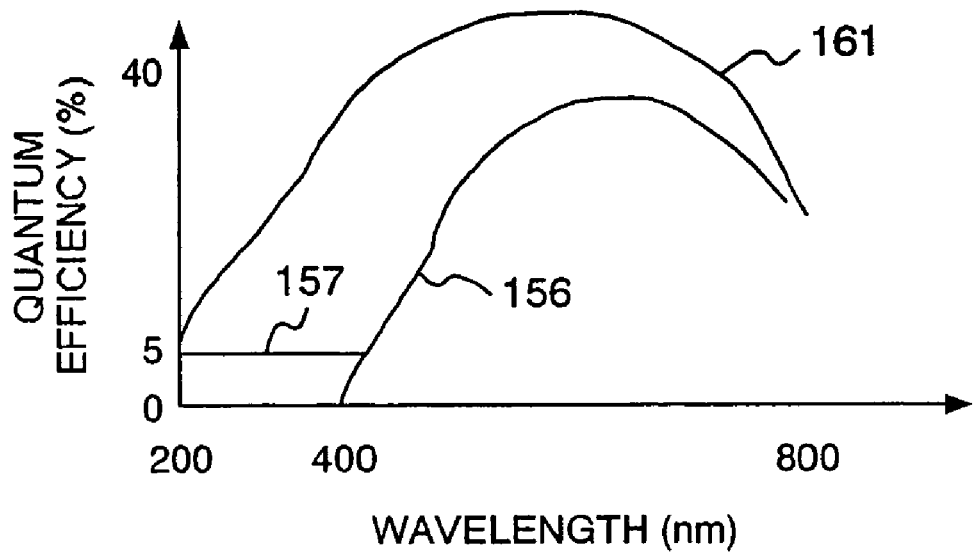
FIG. 23 is also a view for explanation about the characteristic curve of the TDI image sensor, according to the present invention.

FIG. 23 shows the spectral characteristics or properties. A spectral characteristic 156 depicts that of an ordinary surface irradiation type image sensor 200. It has no sensitivity to the lights having wavelength shorter than 400 nm. A spectral characteristic 157 depicts that of the image sensor 201 of organic thin-film coating type. It is added with the sensitivity to the lights having wavelength shorter than 400 nm.

Figure 24:
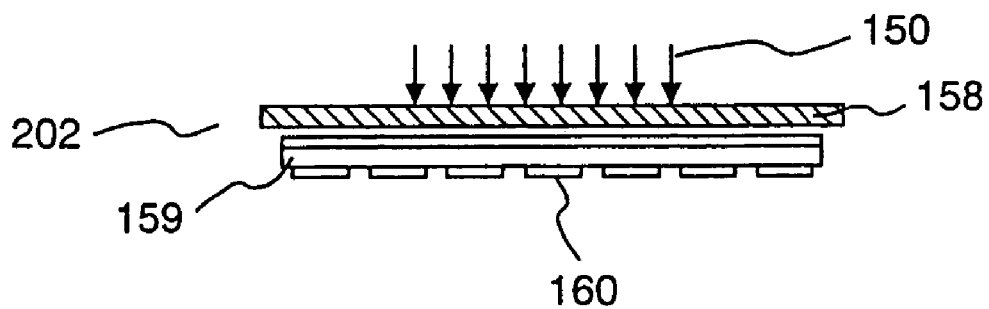
FIG. 24 is a view for explanation on another TDI image sensor, according to the present invention.

For further improving the sensitivity to the DUV light, it is preferable to adopt an image sensor of reverse-surface irradiation type. FIG. 24 shows the structure of the reverse-surface irradiation type image sensor. The incident light 150 penetrates through the cover glass 151, to be incident upon a reverse-side where no gate structure is built up. For this reason, it shows a spectral characteristic 161, as shown in FIG. 23, because of no passage through the gate 154, therefore it is advantageous for the illumination with the short wavelength lights not reaching to 200 nm; i.e., being high in the quantum efficiency (for example, being 30% or more), being wide in the dynamic range (for example, being 3,000 or more), and being sensitive to the wavelength less than 400 nm. In case of using such the image sensor, it is possible to deal with by means of only one image sensor even if using several wavelengths for the illumination. Also, using the TDI (Time Delay Integration) type of the image sensor 201 enables to increase the sensitivity. Further, letting to have the characteristic of anti-blooming enables to dissolve the problem that electric charge flows out into peripheral pixels when obtaining the detection of light being much more than necessary in an amount.

Figure 25:
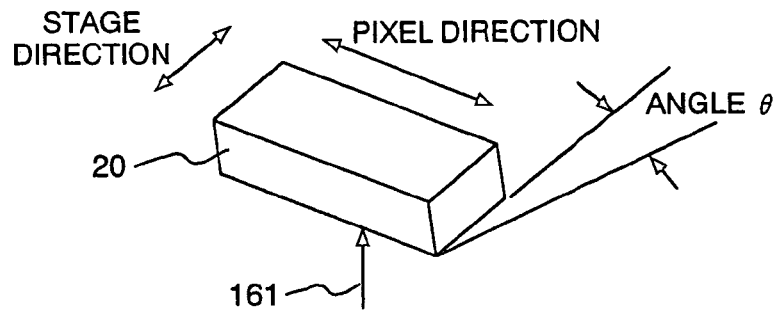
FIG. 25 is a view for explanation about attachment of the TDI image sensor, according to the present invention.

Next, explanation will be given on the installation or attachment of the image sensor 20. FIG. 25 shows a method for attaching the sensor. As was mentioned previously, since it includes the cover glass, the image sensor 20 has a possibility that the interference pattern is generated upon the glass surface. Inclination of the sensor 20 by an angle θ in the direction of the number of stages thereof enables to prevent the interference pattern from generating due to the interference of the laser beam, while generating the deviation in the focus in the direction of pixels.

Further, in addition to the high resolution by means of the UV light, an explanation will be given on a method for improving the pattern contrast, through controlling the polarizing elements group 13, as was mentioned previously. For the purpose of increasing the pattern contrast, by paying attention to the fact that the polarization condition of the UV light can be controlled freely upon the basis of the control of the polarizing elements group 13, the direction of polarization of the illumination light, i.e., the elliptical ratio is controlled, thereby enabling the detection of a part of polarized light elements of the detected light by means of the image sensor 20. As characteristics of the illumination by the UV light, there are facts that it has a single wavelength, and that it is a linearly polarized or plane polarized light. For this reason, it is possible to control the polarization condition, with high efficiency, by means of the polarizing elements group 13, including a ½ wavelength plate and a ¼ wavelength plate provided within the optical path. The control can be achieved by rotating the ½ wavelength plate and/or the ¼ wavelength plate. Since the pattern contrast changes greatly depending upon the polarization condition of illumination, performances of the optical system can be improve, by bringing the polarization condition to be controllable (i.e., positioning by rotation of the wavelength plate(s)). In more details, the linearly polarized light can be controlled in the direction by means of the ½ wavelength plate, while the elliptical ratio by means of the ¼ wavelength plate. With this, it is possible to obtain an improvement of the detection sensitivity. With combination of those, it is also possible to achieve the horizontal Nicol and the vertical Nical. Of course, it is also possible to achieve the circularly polarized light. However, those do not depend upon the illumination wavelength itself. Also, if such an idea mentioned above can be established, the structure may be in any kind for achieving it. Of course, a spatial filter may be disposed at the position being conjugate with the pupil of the objective lens 14, thereby attenuating the $0^{th}$ dimensional light (or, it may be possible to guide the scattered light from the foreign matter into the image sensor, through blocking the diffracted light from the pattern by means of the spatial filter). However, controlling the polarized light enables more effective extraction of the diffracted light therefrom. According to experiments made by the present inventors, it is clear that the contrast can be improved by about 20%-300%. Also, an analyzer (not shown in the figure) may be positioned between the sample 1 and the image sensor 20, to be controlled on rotation thereof, thereby detecting the image of the sample from the reflection light while controlling the polarization condition in the detection optical system.

As was explained in the above, using the DUV light, such as that having wavelength of 266 nm, 248 nm or 192 nm, enables the detection of defects on the device, being under less than 0.07 μm rule. Also, it can be applied to the inspection of Cu damascene, as a target to be inspected, Further, the inspection can be made even onto a portion where no pattern is formed on the target to be inspected, since no erroneous information is produced when comparing between the detected image and the reference image because of no generation of speckles.

However, with the UV light less than 365 nm in wavelength, to be used as the illumination light, since it has high optical energy, contaminants, such as of organic material or the like, are decomposes or react upon due to the energy thereof when the UV light is irradiated upon the optical elements, thereby attaching or adhering upon the surface thereof. For this reason, with provision of a means for discharging air compellingly upon the surface of the optical system by a manner not shown in the figure, and/or a means for puffing air compulsively thereupon, it is possible to prevent the optical parts from deterioration thereof.

Moreover, in the present embodiment, the explanation was given only on the structure of the light-field optical system, however it is also possible to obtain a similar effect if applying the structure of a co-focal microscope into the detection optical system.

According to the present invention mentioned in the above, it is possible to obtain a UV or DUV illumination of high brightness, thereby enabling a pick-up of image with high resolution in short time-period, and as a result, it is possible to obtain an inspection apparatus with high speed and high sensitivity. The defects on patterns detected are outputted with information of the positions and sizes thereof. In particular, the target (the sample) 1 to be inspected mentioned above includes the damascene, of such as Cu, etc., being formed by burying conductive metal, such as Cu, etc., into openings and/or grooves for via (or contac) -holes and/or wirings formed on the insulator film, such as of $SiO_2$, and thereafter removing excess portion deposited or accumulated through polishing by means of CMP, etc. Accordingly, the inspecting method and the apparatus thereof, according to the present invention, can be applied to the damascene of, such as Cu, etc. Also, the inspecting method and the apparatus thereof, according to the present invention, in particular using the DUV light (the light having wavelength of 266 nm, 248 nm, or 193 nm), can be applied very effectively, to the device under the designing rule of 0.07 μm, since it can detects super microscopic or minute defects less than 0.07 μm in size.

Also, according to the present invention, in the method for inspecting the defects on patterns formed on the sample, the UV laser beam is irradiated upon the sample surface, which is lowered in the coherency thereof, and then the image or video signal is processed, being obtained via image pick-up upon the surface of the sample, upon which this UV laser beam is irradiated, therefore it is possible to detect the defects less than 100 nm on the sample, and thereby to obtain information relating to the positions on the sample about the detected defects less than 100 nm.

And also, according to the present invention, the defects less than 100 nm can be detected, on patterns formed on the wafer having a diameter of 200 mm, with throughput of three (3) pieces per one (1) hour.

And further, according to the present invention, it is possible to obtain an effect that an image can be obtained with much higher sensitivity and higher speed, being equal or superior to that obtained under the ordinary discharge tube illumination, by means of the laser beam source, under illumination of short-wavelength necessary for high resolution, and further being able to achieve the and being advantageous for an actual practice thereof, thereby enabling the detection of microscopic defects with high sensitivity.

The invention may be embodied in other specific forms without departing from the spirit or essential characteristics or features thereof. The present embodiment is therefore to be considered in all aspects as illustrative and not restrictive, the scope of the present invention being indicated by the appended claims rather than by the foregoing description and all changes which come within the meaning and range of equivalency of the claims are therefore intended to be embraced therein.

What is claimed is:

1. An apparatus for inspecting pattern defects, comprising:
a light source for emitting an ultraviolet light;
a light beam shape switching unit for switching a shape of the ultraviolet light;
an illumination system for irradiating the ultraviolet light onto a sample;
an image-former for forming an image of reflection light reflected from the sample by the irradiation of the ultraviolet light from the illumination system;
a detector which includes a time delay integration image sensor for receiving the image of the reflection light and for converting it into a detected image signal;
a monitor which monitors the image formed by the image-former; and
an image processor for detecting defects on patterns formed on the sample in accordance with the detected image signal;
wherein the light beam shape switching unit switches the shape of the ultraviolet light to change an illumination area on the sample irradiated by the ultraviolet light to a slit illumination area on the sample which is longer in one direction on the sample when receiving the image detected by the detector and to a wide illumination area on the sample which is larger than the slit area on the sample when monitoring the image by the monitor.

2. The apparatus according to claim 1, wherein the light source includes a laser.

3. The apparatus according to claim 1, wherein the illumination system includes a polarizer for irradiating the sample with a polarized ultraviolet light.

4. The apparatus according to claim 1, wherein the image-former includes an analyzer to adjust a polarization state of the reflection light.

5. The apparatus according to claim 1, wherein the switching unit switches the shape of the ultraviolet light to irradiate the illumination area on sample by controlling movement of at least one member within an irradiation path of the ultraviolet light to the sample so as to irradiate the slit illumination area longer in one direction on the sample when receiving the image detected by the detector and to irradiate the sample in the wide illumination area larger than the slit illumination area when monitoring the image by the monitor.

6. The apparatus according to claim 5, wherein the switching unit controls movement of the at least one member so as to irradiate the sample with the wide area which is a rectangular area larger than the slit area when monitoring the image with the monitor.

7. The apparatus according to claim 6, wherein the at least one member is a homogenizer.

8. The apparatus according to claim 6, wherein the switching unit controls movement of the at least one member so as to irradiate the sample with the wide area which is a rectangular area larger than the slit area when monitoring the image with the monitor.

9. The apparatus according to claim 7, wherein the at least one member is a homogenizer.

10. The apparatus according to claim 1, wherein the light beam shaped switching unit changes the illumination area on the sample to the slit area when receiving the image detected by the detector including the time delay integration sensor, and switches to the wide illumination area on the sample when monitoring the image by the monitor.

11. An apparatus for inspecting pattern defects; comprising:
a light source for emitting an ultraviolet light;
a light beam switching unit for switching the ultraviolet light;
an illumination system for irradiating the ultraviolet light onto a sample;
an image-former for forming an image of the sample with a light reflected from the sample by the irradiation of the ultraviolet light;
a monitor which monitors the image formed by the image-former;
a detector which detects the image formed by the image-forming with a time delay integration image sensor and outputting an image signal; and
an image processor for detecting defects on patterns formed on the sample by processing the image signal outputted from the detector;
wherein the light beam switching unit switches an illumination area on the sample through the illumination system in accordance with detection of the image by the detector and in accordance with monitoring of the image by the monitor.

12. The apparatus according to claim 11, wherein the light source includes a laser.

13. The apparatus according to claim 11, wherein the illumination system includes a polarizer for irradiating the sample with a polarized ultraviolet light.

14. The apparatus according to claim 11, wherein the image-former include an analyzer to adjust a polarization stage of the reflection light.

15. The apparatus according to claim 11, wherein the switching unit switches the shape of the ultraviolet light to irradiate the illumination area on the sample by controlling movement of at least one member within an irradiation path of the ultraviolet light to the sample so as to irradiate a slit illumination area longer in one direction on the sample when detecting the image by the detector and to irradiate the sample in a wide illumination area larger than the slit illumination area when monitoring the image by the monitor.

16. The apparatus according to claim 11, wherein the light beam switching unit switches the illumination area on the sample so as to concentrate a density of the ultraviolet light irradiating the sample in a slit illumination area longer in one direction on the sample when receiving the image detected by the detector and switches the illuminating area on the sample to a wide illumination area larger than the slit illumination area so as to diffuse the density of the ultraviolet light when monitoring the image by the monitor.

17. A method for inspecting pattern defects, comprising the steps of:
illuminating a sample with an ultraviolet light;
forming an image of the sample with a light reflected from the sample illuminated by the ultraviolet light;
detecting the image formed by the light reflected from the sample with a time delay integration sensor and outputting an image signal;
monitoring the image formed by the light reflected from the sample; and
processing the image signal output from the time delay integration sensor and detecting defects on patterns formed on the sample;
wherein in the step of illuminating the sample, an illumination area on the sample is switched in accordance with detection of the image with the time delay integration sensor and in accordance with the monitoring of the image; and wherein in the step of illuminating the sample, the illumination area is switched to be a slit illumination area longer in one direction on the sample when detecting the image with the time delay integration sensor and to be a wide illumination area which is larger than the slit illumination area on the sample when monitoring the image.

18. The method according to claim 17, wherein in the step of illuminating, the ultraviolet light is a laser.

19. The method according to claim 17, wherein in the step of illuminating, the ultraviolet light is a polarized light.

20. The method according to claim 17, wherein in the step of detecting the image, the light reflected from the sample to form the image is adjusted in a polarization state.

21. The method according to claim 17, wherein in the step of illuminating the sample, the illumination area is switched to be a slit illumination area longer in one direction on the sample when detecting the image with the time delay integration sensor and to be a wide illumination area which is larger than the slit illumination area on the sample when monitoring the image.

22. The method according to claim 17, wherein the illumination area on the sample is switched by controlling movement of at least one member within an irradiation path of the ultraviolet light to the sample.

* * * * *

UNITED STATES PATENT AND TRADEMARK OFFICE
CERTIFICATE OF CORRECTION

PATENT NO. : 7,489,395 B2  
APPLICATION NO. : 11/518195  
DATED : February 10, 2009  
INVENTOR(S) : Yoshida et al.

Page 1 of 1

It is certified that error appears in the above-identified patent and that said Letters Patent is hereby corrected as shown below:

Title Page Item (73) should read

(73) Assignee: Hitachi, Ltd., Tokyo (JP)

Signed and Sealed this
Eleventh Day of January, 2011

David J. Kappos
*Director of the United States Patent and Trademark Office*